United States Patent [19]

Willms

[11] Patent Number: 4,725,679

[45] Date of Patent: Feb. 16, 1988

[54] A PROCESS FOR PRODUCING 2-AMINO-ALKENYLSULFONYLUREA DERIVATIVES

[75] Inventor: Lothar Willms, Unkel, Fed. Rep. of Germany

[73] Assignee: Hoechst Aktiengesellschaft, Frankfurt am Main, Fed. Rep. of Germany

[21] Appl. No.: 828,082

[22] Filed: Feb. 7, 1986

Related U.S. Application Data

[63] Continuation-in-part of Ser. No. 643,016, Aug. 22, 1984, abandoned.

[30] Foreign Application Priority Data

Aug. 25, 1983 [DE] Fed. Rep. of Germany ....... 3330603

[51] Int. Cl.$^4$ ............... C07D 223/02; C07D 237/02; C07D 239/02; C07D 241/02
[52] U.S. Cl. ............................. 540/546; 540/553; 540/575; 540/596; 540/600; 544/63; 544/88; 544/96; 544/296; 544/298; 544/320; 544/332; 544/400; 546/233; 548/215; 548/240; 548/352; 548/379; 548/567; 564/40
[58] Field of Search ............. 544/296, 298, 320, 321, 544/332, 63, 88, 96, 400; 540/546, 553, 575, 596, 600; 546/233; 548/215, 240, 352, 379, 567; 564/40

[56] References Cited

U.S. PATENT DOCUMENTS

| 2,184,279 | 12/1939 | Christiansen | 564/95 |
| 3,983,107 | 9/1976 | Holland | 260/240 J |
| 4,062,960 | 12/1977 | Holland | 424/258 |

FOREIGN PATENT DOCUMENTS

| 0098569 | 1/1984 | European Pat. Off. | 544/332 |
| 0015962 | 1/1983 | Japan | 544/332 |

OTHER PUBLICATIONS

Morrison et al., *Organic Chemistry* "Textbook", Allyn and Bacon, Inc., Boston, Mass., 1978, p. 187.
March, *Advanced Organic Chemistry*, "Textbook", McGraw-Hill Book Company, N.Y., N.Y., 1977, p. 742.

*Primary Examiner*—Alan L. Rotman
*Assistant Examiner*—J. G. Mullins
*Attorney, Agent, or Firm*—Curtis, Morris & Safford

[57] ABSTRACT

The novel 2-amino-alkenylsulfonylureas of the formula (I)

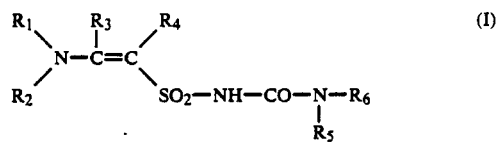

in which
R$_1$ and R$_2$ denote hydrogen, alkyl, cycloalkyl or (substituted) phenyl, or R$_1$ and R$_2$, together with the common nitrogen atom, form a 5-membered to 7-membered (hetero)aliphatic ring, R$_3$ denotes hydrogen, cycloalkyl, alkyl, alk(en)(yn)yloxy, alkylsulfen(in)(on)yl, —SO$_2$ (N)(mono- or di-alkyl), (substituted) phenyl, benzyl, substituted hydroxycarbonyl or (substituted) aminocarbonyl, R$_4$ has the meaning of R$_3$ and additionally denote formyl, alkanoyl, (substituted) benzoyl, cycloalkylcarbonyl or C$_6$H$_5$—CH$_2$—O—CO—, or R$_3$ and R$_4$, together with the olefinic carbon atoms connecting them, form a 5-membered to 8-membered aliphatic ring system, R$_5$ denotes H, alkyl, alkenyl, alkynyl, alkoxy or alkoxycarbonyl and R$_6$ denotes alkyl or cycloalkyl, (substituted) phenyl or a (substituted) pyrimidinyl or (substituted) triazinyl ring, are useful intermediates for the preparation of plant protection agents.

10 Claims, No Drawings

A PROCESS FOR PRODUCING 2-AMINO-ALKENYLSULFONYLUREA DERIVATIVES

This application is a continuation-in-part of application Ser. No. 643,016, filed Aug. 22, 1984, now abandoned.

It is known that chlorosulfonylureas can be reacted with primary and secondary amines to give aminosulfonylureas, HCl being split off (cf. R. Graf, Angew. Chemie, Int. Ed. Engl. 7, 172 (1968); German Patent No. 940,292, equation 1).

Surprisingly, it has now been found that the reaction of halogenosulfonylureas with enamines which carry a hydrogen atom in the β-position relative to the amino group gives high yields of 1,2-unsaturated alkenylsulfonylureas. Novel 2-amino-alkenylsulfonylureas can be prepared in this manner.

The present invention thus relates to novel 2-amino-alkenylsulfonylureas of the formula (I)

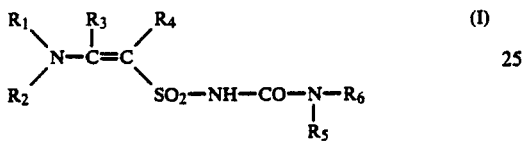

in which
R$_1$ and R$_2$ independently of one another denote hydrogen, (C$_1$–C$_8$)-alkyl, (C$_3$–C$_7$)-cycloalkyl, or phenyl, which can optionally be monosubstituted or polysubstituted by halogen, (C$_1$–C$_4$)-alkyl, (C$_1$–C$_4$)-alkoxy, (C$_1$–C$_4$)-alkylthio, (C$_1$–C$_4$)-alkoxycarbonyl, CF$_3$, NO$_2$ or CH$_3$SO$_2$—, or the radicals R$_1$ and R$_2$, together with the common nitrogen atom, form a 5-membered to 7-membered aliphatic ring, in which one CH$_2$ group can optionally be replaced by oxygen, NH or N(C$_1$–C$_4$)-alkyl, R$_3$ denotes hydrogen, (C$_3$–C$_7$)cycloalkyl, (C$_1$–C$_6$)alkyl, (C$_1$–C$_4$)alkoxy, (C$_2$–C$_4$)alkenyloxy, (C$_2$–C$_4$)alkynyloxy, (C$_1$–C$_4$)alkylsulfenyl, (C$_1$–C$_4$)alkylsulfinyl, (C$_1$–C$_4$)alkylsulfonyl, —SO$_2$NH(C$_1$–C$_4$)alkyl, —SO$_2$N[(C$_1$–C$_4$)alkyl]$_2$, a phenyl radical which is optionally monosubstituted or polysubstituted by halogen CF$_3$, (C$_1$–C$_4$)alkyl, (C$_1$–C$_4$)alkoxy, (C$_1$–C$_4$)alkoxycarbonyl, (C$_1$–C$_4$)alkylsulfenyl, (C$_1$–C$_4$)alkylsulfinyl or (C$_1$–C$_4$)-alkylsulfonyl, or benzyl, (C$_1$–C$_4$)alkoxycarbonyl, (C$_2$–C$_4$)alkenyloxycarbonyl, (C$_2$–C$_4$)alkynyloxycarbonyl, aminocarbonyl, (C$_1$–C$_4$)alkylaminocarbonyl or [(C$_1$–C$_4$)alkyl]$_2$aminocarbonyl, R$_4$ has the meaning of R$_3$ and additionally denotes formyl, (C$_1$–C$_6$)-alkanoyl, benzoyl which can optionally be substituted by halogen, (C$_1$–C$_4$)alkyl, (C$_1$–C$_4$)alkoxy, (C$_1$–C$_4$)alkylthio, CF$_3$, NO$_2$ or (C$_1$–C$_4$)alkoxycarbonyl, or (C$_3$–C$_7$)cycloalkylcarbonyl or C$_6$H$_5$—CH$_2$—O—CO—, or R$_3$ and R$_4$ together with the olefinic carbon atoms connecting them form a 5-membered to 8-membered aliphatic ring system, R$_5$ denotes hydrogen, (C$_1$–C$_6$)-alkyl, (C$_1$–C$_4$)alkenyl, (C$_1$–C$_4$)-alkynyl, (C$_1$–C$_4$)-alkoxy or (C$_1$–C$_4$)-alkoxycarbonyl, R$_6$ denotes (C$_1$–C$_8$)-alkyl or (C$_3$–C$_7$)-cycloalkyl, phenyl which can optionally be monosubstituted or polysubstituted by halogen, (C$_1$–C$_4$)-alkyl, (C$_1$–C$_4$)-alkoxy, (C$_1$–C$_4$)-alkylthio, CF$_3$, NO$_2$ or (C$_1$–C$_4$)-alkoxycarbonyl, or the radical

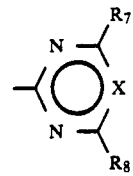

in which
R$_7$ and R$_8$ independently of one another denote hydrogen, (C$_1$–C$_4$)-alkyl or (C$_1$–C$_4$)-alkoxy, which are optionally monosubstituted or disubstituted by (C$_1$–C$_2$)-alkoxy or mono-, di- or tri-substituted by halogen, or halogen, —(CHR$_9$)$_m$—S(O)$_n$R$_{10}$, NH$_2$, NH(C$_1$–C$_4$)-alkyl, N[(C$_1$–C$_4$)-alkyl]$_2$, (C$_2$–C$_4$)-alkenyl, (C$_2$–C$_4$)-alkynyl, (C$_2$–C$_4$)-alkenyloxy or (C$_2$–C$_4$)-alkynyloxy, R$_9$ denotes hydrogen or (C$_1$–C$_4$)-alkyl,
R$_{10}$ denotes (C$_1$–C$_4$)-alkyl or benzyl,
X denotes CH, C-Hal, where Hal=chlorine or bromine, C-(C$_1$–C$_4$)-alkyl, C-(C$_1$–C$_4$)-alkoxy or N,
m denotes a number from zero to three and
n denotes a number from zero to two.

The present invention furthermore relates to a process for the preparation of the compounds of the formula (I) which comprises reacting compounds of the formula (II)

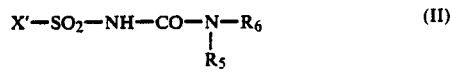

in which X' denotes chlorine or fluorine and R$_5$ and R$_6$ have the abovementioned meanings, with enamines of the formula (III)

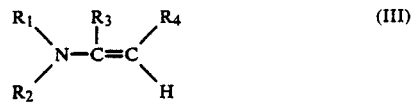

in which R$_1$, R$_2$, R$_3$ and R$_4$ have the abovementioned meanings.

Surprisingly, this process gives high yields of the desired compounds of the formula I, although the enamines of the formula III have various nucleophilic centers and should therefore in principle react in various ways with electrophiles such as the compounds of the formula II (cf. G. Optiz Angew. Chem. 79, 171 (1967)).

The compounds of the formula II are known or are accessible by processes which are known from the literature. They are obtained, for example, by addition of chlorosulfonyl isocyanate onto primary or secondary anilines or amino-heterocyclic compounds (cf. R. Graf, Angew. Chem., Int. Ed. Engl 7, 172 (1968); European Patent Application No. 45,196).

The starting compounds of the formula (III) are prepared by processes which are known from the literature (see, for example, "Enamines-Synthesis, Structure and Reactions", edited by A. G. Cook, M. Dekker Inc., N.Y./London 1969).

The reaction of the compounds (II) and (III) is preferably carried out in inert aprotic solvents, such as, for example, acetonitrile, halogenated aliphatics, such as methylene chloride, hydrocarbons, such as toluene or xylene, or heterocyclic compounds, such as tetrahydrofuran or dioxane, at temperatures between −78° C. and the boiling point of the solvent. The molar ratio of the reaction components is not critical and can be varied within wide limits with a suitable experimental procedure.

The compounds of the formula I are preferably synthesized in the presence of an acid acceptor. Possible acid acceptors are: inorganic compounds, such as, for example, alkali metal carbonates, bicarbonates, oxides or hydroxides and alkaline earth metal carbonates, bicarbonates, oxides or hydroxides, or organic bases, such as aliphatic or cycloaliphatic tertiary amines, such as, for example, triethylamine or N,N-diisopropylamine, or nitrogen-containing aromatics, such as, for example, pyridine or 2,6-lutidine. The enamine component (III) can also be used as the auxiliary base, and is then employed in excess, preferably at a molar ratio of III:II of 1.8 to 2.4:1.

The 2-amino-alkenylsulfonylureas of the general formula (I) according to the invention are useful intermediates for the synthesis of novel plant protection agents and pharmaceuticals.

Thus, for example, when (I) is reacted with 1,2-dinucleophiles, heterocyclic sulfonylureas with herbicidal properties are obtained; see German Patent Application P No. 3,330,602.8.

The compounds of the formula (I) according to the invention furthermore in some cases themselves have herbicidal and plant growth-regulating activities.

The following examples serve to illustrate the invention.

EXAMPLE 1

Ethyl 2-[3-(4,6-dimethyl-2-pyrimidinyl)-ureidosulfonyl]-3-methylamino-2-butenoate 12.7 g (0.1 mole) of 2-amino-4,6-dimethylpyrimidine were added to 9.2 ml (0.105 mole) of CSI[(1)] in 250 ml of anhydrous methylene chloride at −70° C. in the course of about 5 minutes, under nitrogen. The reaction mixture was allowed to warm to 0° C. in the course of about 1 hour and was then cooled to −70° C., and 28.6 g (0.2 mole) of ethyl β-methylaminocrotonate (dissolved in about 50 ml of anhydrous methylene chloride) were then added in the course of 1 hour. The reaction mixture was allowed to warm to room temperature and was subsequently stirred for 18 hours and extracted four times with water, and the product was precipitated with n-hexane.

[(1)]CSI=chlorosulfonyl isocyanate

Yield: 32.6 g (88% of theory). Melting point: 177°-180° C.

EXAMPLE 2

N-[(4,6-Dimethylpyrimidin-2-yl)aminocarbonyl]-1-methylcarbonyl-2-methylamino-prop-1-en-1-yl-sulfonamide 12.3 g (0.1 mole) of 2-amino-4,6-dimethylpyrimidine were added to 9.2 ml (0.105 mole) of CSI in 250 ml of absolute methylene chloride at −70° C. in the course of about 5 minutes, under a nitrogen atmosphere. The reaction mixture was allowed to warm to 0° C. in the course of 1 hour and was cooled to −70° C., and 11.4 g (0.1 mole) of 4-methylamino-but-3-en-2-one (dissolved in 50 ml of $CH_2Cl_2$) and 10.1 g (0.1 mole) of $Et_3N$ were then added dropwise in succession. The reaction mixture was allowed to warm to room temperature in the course of about 4 hours and was stirred at room temperature for 18 hours, extracted four times with 150 ml of water each time and dried over sodium sulfate. n-Hexane was then added dropwise to the mixture at 0° C. The product which had precipitated was filtered off with suction and dried in vacuo. Melting point: 192° C. Yield: 29.3 g (86% of theory).

EXAMPLE 3

Methyl 2-[3-(4,6-dimethyl-2-pyrimidinyl)-ureidosulfonyl]-3-amino-2-butenoate 12.3 g (0.1 mole) of 2-amino-4,6-dimethylpyrimidine were added to 9.2 ml (0.105 mole) of CSI in 250 ml of anhydrous methylene chloride at −70° C. in the course of about 5 minutes, under a nitrogen atmosphere. The mixture was allowed to warm to 0° C. in the course of 1 hour and was then cooled to −70° C., and 23.0 g (0.2 mole) of methyl β-aminocrotonate (dissolved in 100 ml of anhydrous methylene chloride) were added dropwise in the course of 2 hours. After the mixture had been subsequently stirred at room temperature for 18 hours, it was extracted four times with water and the insoluble residue was filtered off with suction. 24.6 g (72% of theory) of the desired product of melting point 222°-225° C. were obtained.

7.0 g (20.4% of theory) of methyl 3-[(3-(4,6-dimethyl-2-pyrimidinyl)ureidosulfonylamino]-2-butenoate were isolated as a by-product from the methylene chloride filtrate, after drying over sodium sulfate and addition of n-hexane. Melting point: 139°-140° C. (decomposition).

The sulfonylurea derivatives of the formula I listed in Table 1 were prepared in the same manner.

TABLE 1

| Compound No. | $R_1$ | $R_2$ | $R_3$ | $R_4$ | $R_5$ | $R_6$ | Melting point (°C.) |
|---|---|---|---|---|---|---|---|
| 4 | H | H | $CH_3$ | $COOC_2H_5$ | H | 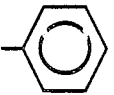 | 159–160 |
| 5 | H | H | $CH_3$ | $COOCH_3$ | H | 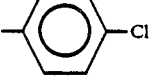 | |

TABLE 1-continued
| Compound No. | R₁ | R₂ | R₃ | R₄ | R₅ | R₆ | Melting point (°C.) |
|---|---|---|---|---|---|---|---|
| 6 | CH₃ | CH₃ | 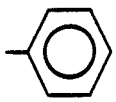 | COOCH₃ | H | 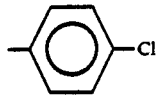 4-Cl | |
| 7 |  | H | 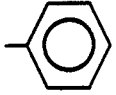 | COOC₂H₅ | CH₃ | 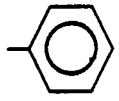 | |
| 8 | —(CH₂)₄— | | CH₃ | COOCH₃ | H | 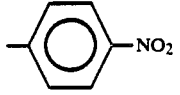 4-NO₂ | |
| 9 | C₂H₅ | H | CH₃ | COOCH₃ | H | 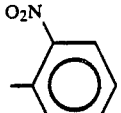 3-NO₂ | |
| 10 | nC₃H₇ | H | CH₃ | COOCH₃ | H | 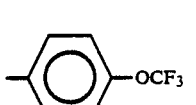 4-OCF₃ | |
| 11 | CH₃ | H | CH₃ | CO | H | 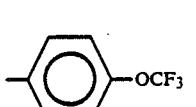 4-OCF₃ | |
| 12 | CH₃ | CH₃ | C₂H₅ | COOCH₃ | H | 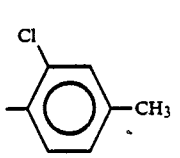 2-Cl, 4-CH₃ | |
| 13 | —(CH₂)₂—O—(CH₂)₂— | | | —(CH₂)₄— | H | 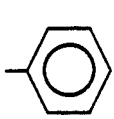 | |
| 14 | —(CH₂)₂—O—(CH₂)₂— | | | —(CH₂)₃— | H | 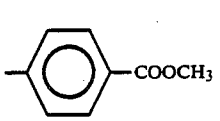 4-COOCH₃ | |
| 15 | (CH₂)₂N(CH₃)—(CH₂)₂— | | | —(CH₂)₄— | H | 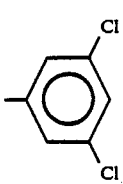 2,4-Cl₂ | |
| 16 | 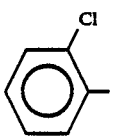 2-Cl | H | H | COOC₂H₅ | H | 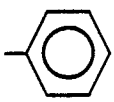 | |
| 17 | —(CH₂)₂—O—(CH₂)₂— | | H | 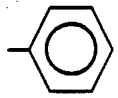 | H | 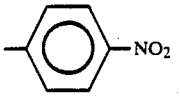 4-NO₂ | |

TABLE 1-continued

| Compound No. | R₁ | R₂ | R₃ | R₄ | R₅ | R₆ | Melting point (°C.) |
|---|---|---|---|---|---|---|---|
| 18 | 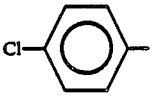 4-Cl-C₆H₄ | H | CH₃ | COCH₃ | H | 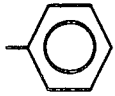 C₆H₅ | |
| 19 | CH₃ | H | CH₃ | COOC₂H₅ | H | 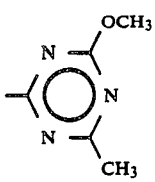 4-OCH₃-6-CH₃-1,3,5-triazin-2-yl | 168 |
| 20 | CH₃ | CH₃ | CH₃ | COOC₂H₅ | H | 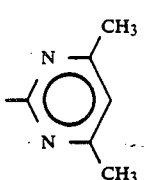 4,6-diCH₃-pyrimidin-2-yl | 161 |
| 21 | CH₃ | CH₃ | CH₃ | COOC₂H₅ | H | 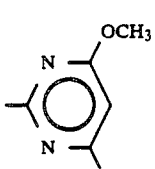 4-OCH₃-6-CH₃-pyrimidin-2-yl | 159–161 |
| 22 | H | H | CH₃ | COOC₂H₅ | H | 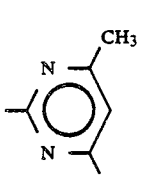 4,6-diCH₃-pyrimidin-2-yl | 180 |
| 23 | CH₃ | H | CH₃ | COOCH₃ | H | 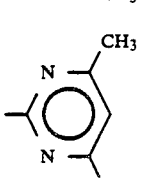 4,6-diCH₃-pyrimidin-2-yl | 175 |
| 24 | CH₃ | H | CH₃ | COOC₂H₅ | H | 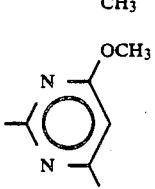 4-OCH₃-6-CH₃-pyrimidin-2-yl | 169–171 |
| 25 | CH₃ | H | CH₃ | COOC₂H₅ | H | 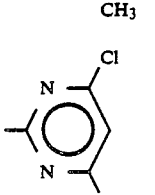 4-Cl-6-CH₃-pyrimidin-2-yl | 169–171 |
| 26 | CH₃ | H | CH₃ | COOC₂H₅ | H | 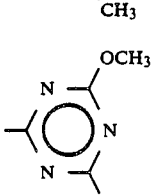 4,6-diOCH₃-1,3,5-triazin-2-yl | 190 |

TABLE 1-continued
| Compound No. | R₁ | R₂ | R₃ | R₄ | R₅ | R₆ | Melting point (°C.) |
|---|---|---|---|---|---|---|---|
| 27 |  | H | CH₃ | COOC₂H₅ | H | 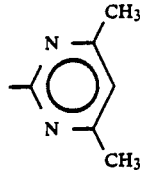 | 114 |
| 28 | CH₃ | H | CH₃ | COOC₂H₅ | C₂H₅ | 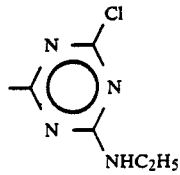 | 147 |
| 29 | CH₃ | CH₃ | CH₃ | COOC(CH₃)₃ | H | 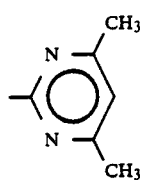 | 140–143 |
| 30 | CH₃ | H | CH₃ | COOC₂H₅ | H | 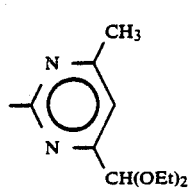 | 135–148 |
| 31 | —(CH₂)₂—O—(CH₂)₂— | | | —(CH₂)₄— | H | 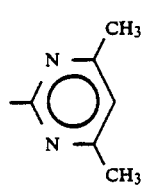 | resin |
| 32 | CH₃ | H | CH₃ | COCH₃ | H | 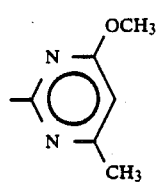 | 159–161 |
| 33 | CH₃ | H | CH₃ | COCH₃ | H | 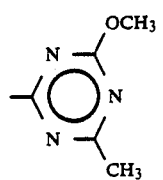 | 156 |
| 34 | H | H | CH₃ | COCH₃ | H | 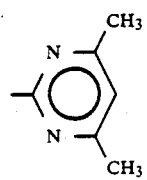 | 210–212 |

TABLE 1-continued

| Compound No. | $R_1$ | $R_2$ | $R_3$ | $R_4$ | $R_5$ | $R_6$ | Melting point (°C.) |
|---|---|---|---|---|---|---|---|
| 35 | phenyl | H | $CH_3$ | $COCH_3$ | H | 4,6-dimethylpyrimidin-2-yl | 149–151 |
| 36 | phenyl | H | phenyl | $COCH_3$ | H | 4,6-dimethylpyrimidin-2-yl | 157–159 |
| 37 | $CH_3$ | H | phenyl | $COCH_3$ | H | 4,6-dimethylpyrimidin-2-yl | 146–148 |
| 38 | $CH_3$ | H | $CH_3$ | $COCH_3$ | H | 4-methyl-6-dimethoxymethyl-pyrimidin-2-yl | 167–169 |
| 39 | $CH_3$ | H | $C_6H_5-CO-C_6H_4-$ | | H | 4-methoxy-6-methyl-pyrimidin-2-yl | |
| 40 | $CH_3$ | $CH_3$ | $CH_3$ | $COOCH_2C_6H_5$ | H | 4,6-dimethoxypyrimidin-2-yl | |
| 41 | $-(CH_2)_4-$ | | $CH_3$ | $COCH_3$ | H | 4-methoxy-6-methyl-pyrimidin-2-yl | |
| 42 | $-(CH_2)_2-O-(CH_2)_2-$ | | $CH_3$ | $COCH_3$ | H | 4,6-dimethoxypyrimidin-2-yl | |
| 43 | $CH_3$ | $CH_3$ | $C_2H_5$ | $COC_2H_5$ | H | 4-methylpyridin-2-yl | |

TABLE 1-continued

| Compound No. | $R_1$ | $R_2$ | $R_3$ | $R_4$ | $R_5$ | $R_6$ | Melting point (°C.) |
|---|---|---|---|---|---|---|---|
| 44 | $CH_3$ | H | $CH_3$ | $COCH_3$ | H | 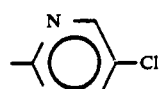 | |
| 45 | $CH_3$ | H | $CH_3$ | $COCH_3$ | H | 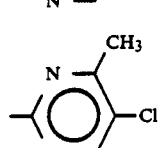 | |
| 46 | H | H | $CCl_3$ | $COOC_2H_5$ | H | 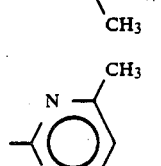 | |

I claim:

1. A process for the preparation of a compound of the formula I

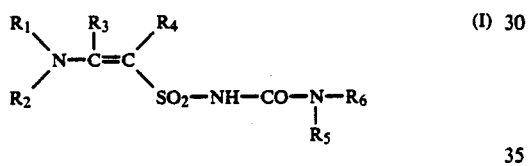

in which $R_1$ and $R_2$ independently of one another are hydrogen, $(C_1-C_8)$-alkyl, $(C_3-C_7)$-cycloalkyl, or phenyl, which are unsubstituted or mono- or polysubstituted by halogen, $(C_1-C_4)$-alkyl, $(C_1-C_4)$-alkoxy, $(C_1-C_4)$-alkylthio, $(C_1-C_4)$-alkoxycarbonyl, $CF_3$, $NO_2$ or $CH_3SO_2-$, or the radicals $R_1$ and $R_2$, together with the common nitrogen atom, form a 5-membered to 7-membered aliphatic ring, in which one $CH_2$ group can optionally be replaced by oxygen, NH or $N(C_1-C_4)$-alkyl, $R_3$ is hydrogen, $(C_3-C_7)$cycloalkyl, $(C_1-C_6)$alkyl, $(C_1-C_4)$alkoxy, $(C_2-C_4)$alkenyloxy, a phenyl radical which is unsubstituted, mono- or polysubstituted by halogen, $CF_3$, $(C_1-C_4)$alkyl, $(C_1-C_4)$alkoxy, $(C_1-C_4)$alkoxycarbonyl, $(C_1-C_4)$alkylsulfenyl, $(C_1-C_4)$alkylsulfinyl or $(C_1-C_4)$-alkylsulfonyl, benzyl, or $(C_1-C_4)$alkoxycarbonyl, $R_4$, independent of $R_3$, has the meaning of $R_3$ and additionally is formyl, $(C_1-C_6)$-alkanoyl, benzoyl which is unsubstituted or substituted by halogen, $(C_1-C_4)$alkyl, $(C_1-C_4)$alkoxy, $(C_1-C_4)$alkylthio, $CF_3$, $NO_2$ or $(C_1-C_4)$alkoxycarbonyl, or $(C_3-C_7)$-cycloalkylcarbonyl or $C_6H_5-CH_2-O-CO-$, or $R_3$ and $R_4$ together with the olefinic carbon atoms connecting them form a 5-membered to 8-membered cycloaliphatic ring, $R_5$ is hydrogen, $(C_1-C_6)$-alkyl, $(C_1-C_4)$alkenyl, $(C_1-C_4)$-alkynyl, $(C_1-C_4)$-alkoxy or $(C_1-C_4)$-alkoxycarbonyl, $R_6$ is $(C_1-C_8)$-alkyl or $(C_3-C_7)$-cycloalkyl, phenyl which is unsubstituted or mono- or polysubstituted by halogen, $(C_1-C_4)$-alkyl, $(C_1-C_4)$-alkoxy, $(C_1-C_4)$-alkylthio, $CF_3$, $NO_2$ or $(C_1-C_4)$-alkoxycarbonyl, or the radical

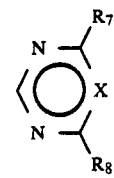

in which $R_7$ and $R_8$ independently of one another are hydrogen, $(C_1-C_4)$-alkyl or $(C_1-C_4)$-alkoxy, which are unsubstituted or mono- or disubstituted by $(C_1-C_2)$-alkoxy or mono-, di- or trisubstituted by halogen, or halogen, $-(CHR_9)_m-S(O)_nR_{10}$, $NH_2$, $NH(C_1-C_4)$-alkyl, $N[(C_1-C_4)$-alkyl$]_2$, $(C_2-C_4)$-alkenyl, $(C_2-C_4)$-alkynyl, $(C_2-C_4)$alkenyloxy or $(C_2-C_4)$-alkynyloxy, $R_9$ is hydrogen or $(C_1-C_4)$-alkyl, $R_{10}$ is $(C_1-C_4)$-alkyl or benzyl, X is CH, C-Hal, where Hal=chlorine or bromine, C-$(C_1-C_4)$-alkyl, C-$(C_1-C_4)$-alkoxy or N, m is a number from zero to three and n is a number from zero to two, which comprises reacting a compound of the formula II

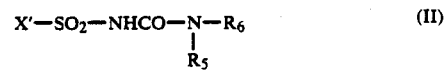

in which X' is chlorine or fluorine and $R_5$ and $R_6$ have the meanings as in formula I, with enamines of the formula III

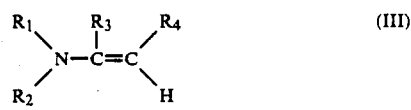

in which $R_1$ to $R_4$ have the meanings as in formula I, in the presence of an acid acceptor and a solvent selected from the group consisting of acetonitrile, a halogenated aliphatic, a hydrocarbon, tetrahydrofuran and dioxane.

2. The process as claimed in claim 1, wherein the reaction is carried out at a temperature of between $-78°$ C. and the boiling point of the solvent.

3. The process as claimed in claim 1, wherein the solvent is selected from the group consisting of methylene chloride, toluene, xylene, tetrahydrofuran and dioxane.

4. The process as claimed in claim 1, wherein the acid acceptor is an inorganic base selected from the group consisting of an alkali metal carbonate, bicarbonate, oxide or hydroxide; or an alkaline earth metal carbonate, bicarbonate, oxide or hydroxide.

5. The process as claimed in claim 1, wherein the acid acceptor is the enamine of formula III used in excess.

6. The process as claimed in claim 1, wherein the acid acceptor is an organic base selected from the group consisting of an aliphatic or cycloaliphatic tertiary amine or a nitrogen-containing aromatic compound.

7. The process as claimed in claim 5, wherein the molar ratio of the enamine of formula III to the compound of formula II is 1.8 to 2.4:1.

8. The process as claimed in claim 6, wherein the organic base is selected from the group consisting of triethylamine, N,N-diisopropylamine, pyridine and 2,6-lutidine.

9. The process as claimed in claim 1, wherein in the compound of formula I, the substituent $R_4$ is H, $(C_1-C_4)$-alkoxycarbonyl, formyl, $(C_1-C_6)$-alkanoyl, benzoyl which is unsubstituted or substituted by halogen, $(C_1-C_4)$alkyl, $(C_1-C_4)$-alkoxy, $(C_1-C_4)$-alkylthio, $CF_3$, $NO_2$ or $(C_1-C_4)$-alkoxycarbonyl, or is $(C_3-C_7)$-cycloalkylcarbonyl or $C_6H_5-CH_2-O-CO-$.

10. The process as claimed in claim 1, wherein the solvent is a halogenated aliphatic solvent and the acid acceptor is an aliphatic tertiary amine.

* * * * *